US009993165B2

(12) United States Patent
Thakur et al.

(10) Patent No.: US 9,993,165 B2
(45) Date of Patent: *Jun. 12, 2018

(54) TRANSIENT SENSOR RESPONSE TO POSTURE AS A MEASURE OF PATIENT STATUS

(71) Applicant: Cardiac Pacemakers, Inc., St. Paul, MN (US)

(72) Inventors: Pramodsingh Hirasingh Thakur, Woodbury, MN (US); Abhilash Patangay, Inver Grove Heights, MN (US); John D. Hatlestad, Maplewood, MN (US); Kenneth C. Beck, Liberty, UT (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 455 days.

This patent is subject to a terminal disclaimer.

(21) Appl. No.: 14/681,267

(22) Filed: Apr. 8, 2015

(65) Prior Publication Data

US 2015/0208928 A1    Jul. 30, 2015

Related U.S. Application Data

(63) Continuation of application No. 13/437,318, filed on Apr. 2, 2012, now Pat. No. 9,066,659.

(60) Provisional application No. 61/473,349, filed on Apr. 8, 2011.

(51) Int. Cl.
| | |
|---|---|
| *G01N 33/48* | (2006.01) |
| *A61B 5/0205* | (2006.01) |
| *A61B 5/00* | (2006.01) |
| *A61B 5/11* | (2006.01) |
| *A61B 5/07* | (2006.01) |
| *G06F 19/00* | (2018.01) |
| *A61N 1/365* | (2006.01) |
| *A61B 5/024* | (2006.01) |

(52) U.S. Cl.
CPC .......... *A61B 5/0205* (2013.01); *A61B 5/0031* (2013.01); *A61B 5/076* (2013.01); *A61B 5/1116* (2013.01); *A61B 5/1118* (2013.01); *A61B 5/4836* (2013.01); *A61B 5/4848* (2013.01); *A61B 5/686* (2013.01); *A61B 5/7246* (2013.01); *A61B 5/7275* (2013.01); *A61B 5/742* (2013.01); *A61B 5/02405* (2013.01); *A61B 2560/0462* (2013.01); *A61B 2562/0219* (2013.01); *A61N 1/36535* (2013.01); *G06F 19/34* (2013.01)

(58) Field of Classification Search
CPC .................................................. A61B 5/0205
USPC ....................................................... 702/19
See application file for complete search history.

(56) References Cited

U.S. PATENT DOCUMENTS

| | | |
|---|---|---|
| 5,800,471 A | 9/1998 | Baumann |
| 7,226,422 B2 | 6/2007 | Hatlestad et al. |
| 7,384,395 B2 | 6/2008 | Hatlestsad et al. |
| 7,422,560 B2 | 9/2008 | Hatlestsad et al. |
| 7,559,901 B2 | 7/2009 | Maile et al. |
| 7,819,804 B2 | 10/2010 | Hatlestad et al. |
| 2008/0082001 A1 | 4/2008 | Hatlestad et al. |
| 2009/0024005 A1 | 1/2009 | Lewicke et al. |
| 2010/0022911 A1 | 1/2010 | Wariar et al. |
| 2010/0113888 A1 | 5/2010 | Cho et al. |
| 2010/0113890 A1 | 5/2010 | Cho et al. |
| 2011/0009709 A1 | 1/2011 | Hatlestsad et al. |
| 2011/0172564 A1 | 7/2011 | Drew |
| 2012/0108915 A1 | 5/2012 | Corbucci et al. |
| 2012/0259183 A1 | 10/2012 | Thakur et al. |

FOREIGN PATENT DOCUMENTS

JP          4514711         7/2010

OTHER PUBLICATIONS

"U.S. Appl. No. 13/437,318, Advisory Action dated Jun. 13, 2014", 3 pgs.
"U.S. Appl. No. 13/437,318, Final Office Action dated Feb. 27, 2014", 8 pgs.
"U.S. Appl. No. 13/437,318, Final Office Action dated Dec. 23, 2014", 7 pgs.
"U.S. Appl. No. 13/437,318, Non Final Office Action dated Aug. 1, 2013", 7 pgs.
"U.S. Appl. No. 13/437,318, Non Final Office Action dated Aug, 28, 2014", 6 pgs.
"U.S. Appl. No. 13/437,318, Notice of Allowance dated Feb. 26, 2015", 8 pgs.
"U.S. Appl. No. 13/437,318, Response filed Feb. 11, 2015 to Final Office Action dated Dec. 23, 2014", 12 pgs.
"U.S. Appl. No. 13/437,318, Response filed Apr. 15, 2014 to Final Office Action dated Feb. 27, 2014", 14 pgs.
"U.S. Appl. No. 13/437,318, Response filed May 14, 2013 to Restriction Requirement dated Apr. 18, 2013", 9 pgs.
"U.S. Appl. No. 13/437,318, Response filed Nov. 26, 2014 to Non Final Office Action dated Aug. 28, 2014", 12 pgs.
"U.S. Appl. No. 13/437,318, Response filed Dec. 2, 2013, to Non Final Office Action dated Aug. 1, 2013", 13 pgs.
"U.S. Appl. No. 13/437,318, Restriction Requirement dated Apr. 18, 2013", 6 pgs.
Averina, Viktoria A, et al., "U.S. Appl. No. 61/423,127, filed Dec. 20, 2010", Physiologic Response to Posture, 50 pgs.
Borst, C., et al., "Mechanisms of initial heart rate response to postural change", Am J Physiol., 243(5), (Nov. 1982), H676-81.

(Continued)

Primary Examiner — Jerry Lin
(74) Attorney, Agent, or Firm — Schwegman Lundberg & Woessner, P.A.

(57) ABSTRACT

Patient posture information can be received, such as to indicate a change in patient posture by at least a threshold amount. A transient response signal indicative of a change in a physiological parameter can be received at multiple instances near a change in patient posture. Waveform morphology features can be extracted from a transient response signal and used to provide an indication of a cardiac status, such as a heart failure status.

20 Claims, 9 Drawing Sheets

(56) References Cited

OTHER PUBLICATIONS

Cheng, J H, "Posture shift alters pattern of heart rate and blood pressure response during valsalva maneuver", English Summary of article in Chinese journal, 3 pgs.
Rossberg, F., et al., "Initial cardiovascular response on change of posture from squatting to standing", Eur J Appl Physio Occup Physiol., 57(1), (1988), 93-7.
Thakur, Pramodsingh Hirasingh, "U.S. Appl. No. 61/423,127, filed Dec. 15, 2010", Cardiac Decompensation Detection Using Multiple Sensors, 71 pgs.
Thakur, Pramodsingh Hirasingh, et al., "U.S. Appl. No. 61/423,128, filed Dec. 15, 2010", Posture Detection Using Thoracic Impedance, 71 pgs.

TRANSIENT SENSOR RESPONSE TO POSTURE AS A MEASURE OF PATIENT STATUS

CLAIM OF PRIORITY

This application is a continuation of U.S. application Ser. No. 13/437,318, filed Apr. 2, 2012, which claims the benefit of priority under 35 U.S.C. § 119(e) of Thakur et al., U.S. Provisional Patent Application Ser. No. 61/473,349, entitled "TRANSIENT SENSOR RESPONSE TO POSTURE AS A MEASURE OF PATIENT STATUS", filed on Apr. 8, 2011, each of which is herein incorporated by reference in its entirety.

BACKGROUND

Cardiac rhythm management devices can include implantable or other ambulatory devices, such as pacemakers, cardioverter-defibrillators, cardiac resynchronization therapy (CRT) devices, or devices that can monitor one or more physiological parameters, or provide one or a combination of pacing, defibrillation, or cardiac resynchronization therapies, or that can both monitor one or more physiological parameters and provide therapy. These devices can be configured for use with multiple physiological parameter sensors, such as including implanted or external electrodes, such as to detect or treat cardiac, respiratory, or other conditions. Information obtained using the sensors can be used to provide a diagnosis, monitor a disease state, or to indicate an initiation or adjustment of therapy, among other functions.

Early detection of physiological conditions that can indicate heart failure ("HF," sometimes referred to as congestive heart failure, "CHF"), such as before a patient experiences cardiac decompensation associated with such heart failure, can help to indicate treatment that may prevent cardiac decompensation from occurring. For example, Hatlestad et al., in U.S. Patent Application No. 2008/0082001, entitled "PHYSIOLOGICAL RESPONSE TO POSTURE CHANGE," refers to sensing a steady state change in a physiological signal as a result of a change in posture, and generating a response. The steady state change in the physiological signal can be used to identify a heart failure condition. The steady state physiological signal can include a heart rate signal, a blood pressure signal, a heart sound energy signal, a heart rate variability signal, or a respiration rate signal.

Accurate and efficient posture detection can help to provide important information to a clinician or a cardiac rhythm management device, such as to ensure accurate interpretation of one or more physiological parameters, or to determine a therapy. Maile et al., in U.S. Pat. No. 7,559,901, entitled DETERMINING A PATIENT'S POSTURE FROM MECHANICAL VIBRATIONS OF THE HEART, refers to determining a patient's posture by monitoring heart sounds. (See Maile et al. at the Abstract.) Patient posture information can also be received from one or more accelerometers, such as can be disposed in or on a patient body, including information about a patient tilt angle. In another example, patient posture information can be discerned from thoracic impedance information, such as by clustering the thoracic impedance information, as described by Thakur et al., in U.S. Patent Application No. 61/423,128, entitled "POSTURE DETECTION USING THORACIC IMPEDANCE."

Some cardiovascular responses corresponding to different patient postural changes are well understood. For example, Rossberg et al., in European Journal of Applied Physiology, vol. 57, page 93 (1988), entitled "INITIAL CARDIOVASCULAR RESPONSE ON CHANGE OF POSTURE FROM SQUATTING TO STANDING," discusses differences in cardiovascular response corresponding to a first postural change from a squatting to a standing posture, and corresponding to a second postural change from a recumbent to a standing posture. For example, Rossberg et al. detected a decrease in systolic, diastolic, and mean pressure during a first heart beat after a posture change.

OVERVIEW

Patient posture information can be received, such as to indicate a change in patient posture by at least a threshold amount. A transient response signal indicative of a change in a physiological parameter can be received at multiple instances near a change in patient posture. Waveform morphology features can be extracted from a transient response signal and used to provide an indication of a cardiac status, such as a heart failure status.

Various electrical or mechanical functions of cardiac or respiratory systems can provide a variety of physiological parameters that can indicate the onset of a condition, for instance, heart failure, arrhythmia (fibrillation, tachycardia, bradycardia), ischemia, or the like. These physiological parameters can include, for example, heart sounds (e.g., S3 amplitude), DC impedance near the lungs, heart rate, respiration rate, or intracardiac pressure, among others. Further examples of a physiological parameter can include, but are not limited to, a blood pressure, a hormone level, a blood count, a neural activity, a muscle activity, a blood oxygen or carbon dioxide concentration, a lung tidal volume, or any other physiological parameter. At least some of these parameters can indicate the onset or change of a condition, and can be used to provide an alert that therapy (or therapy adjustment) is needed, such as defibrillation, a change in pacing, or the like.

This document describes, among other things, systems, methods, machine-readable media, or other techniques, that can involve obtaining physiological data, such as posture change information, or physiological signal information, such as including a transient waveform signal indicative of a physiological response. The systems, methods, machine-readable media, or other techniques can involve extracting information from the transient waveform signal, such as a waveform morphology feature, and providing an indication of a cardiac status, such as using the extracted information, such as by comparing the waveform morphology feature to a metric to determine an indication of worsening heart failure.

The techniques described and illustrated herein can be directed toward diagnosing a patient risk for cardiac decompensation in advance of heart failure. The techniques can involve obtaining physiological data, such as using one or more physiological sensors disposed in or near a patient body, such as at a first time corresponding to a patient posture change. For example, a transient waveform signal indicative of a physiological response can be received in the several seconds following a patient posture change. The techniques can involve extracting one or more waveform morphology features from the signal. The techniques can involve modeling the transient waveform signal, such as using a first or second order system approximation of the transient waveform signal, and extracting one or more characteristic parameters of the model. In an example, the extracted features or characteristic parameters can be used to provide an indication of a cardiac status.

The present techniques, involving a transient signal indicative of a physiological response, can provide one or more disease state indicators that can provide enhanced specificity, such as over other approaches using only steady state physiological information (e.g., a steady state heart rate) to predict cardiac decompensation. Rapid changes in patient physiological status can be captured in a transient response signal, and patient diagnostic information can be extracted from such changes.

The present inventors have recognized, among other things, that a problem to be solved can include providing more sensitive or more specific advance notification of a patient's risk for imminent cardiac decompensation. In an example, the present subject matter can provide a solution to this problem, such as by obtaining a transient response signal indicative of a physiological response, obtaining patient posture change information, extracting one or more waveform morphology features from the transient response signal, and providing advance notification of a patient's risk for cardiac decompensation using the one or more waveform morphology features, such as by trending the one or more waveform morphology features.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
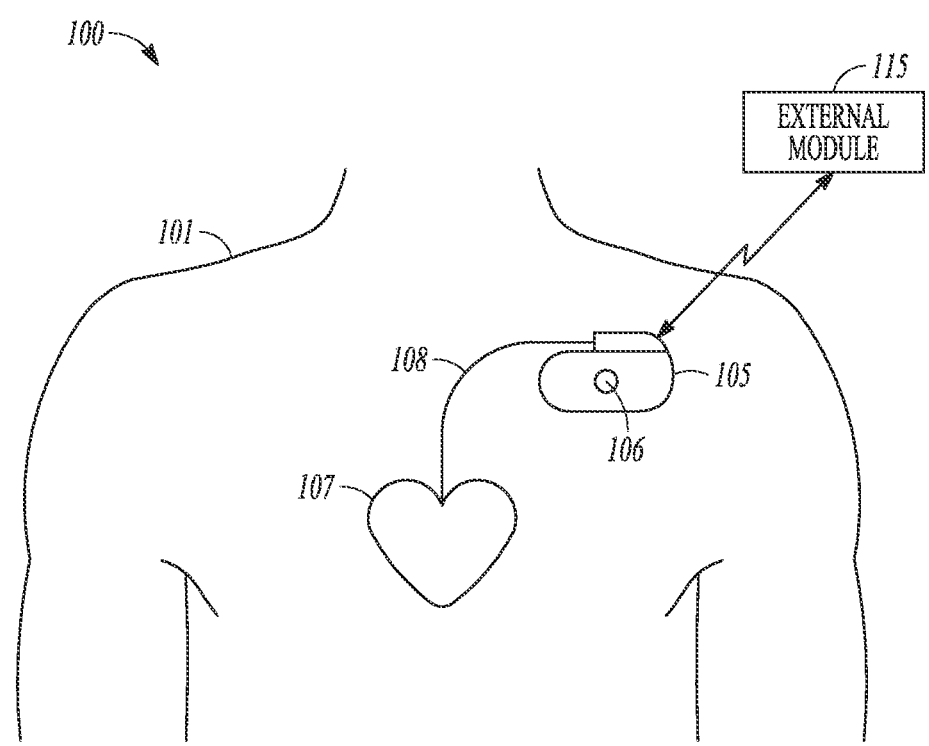
FIG. 1 illustrates generally an example of a portion of a system that can include an implantable medical device, including one or more physiological sensors, communicatively coupled with an external module.

FIG. 1 illustrates generally an example of a system 100 including an ambulatory or implantable medical device (IMD) 105 in a subject body 101, the IMD 105 wirelessly coupled to an external module 115. The IMD 105 can be coupled to a heart 107, such as using a lead system 108, such as an implantable lead system. In an example, the IMD 105 can include one or more of a cardiac stimulating circuit, a cardiac sensing circuit, or a processor circuit. In certain examples, a functional portion of one or more of the cardiac stimulating circuit, cardiac sensing circuit, or the processor circuit can occur in the IMD 105, and another portion elsewhere (e.g., in an external programmer or analyzer circuit).

In an example, the IMD 105 can include a cardiac rhythm management device, such as a pacemaker, or a defibrillator, among other implantable medical devices. In an example, the IMD 105 can include an antenna configured to provide radio-frequency or other communication between the IMD 105 and the external module 115, or other external device.

In an example, the IMD 105 can include a sensor 106, such as within or upon the housing of the IMD 105. In an example, the sensor 106 can include an accelerometer, such as can be configured to detect patient motion, or to detect a patient posture status. Posture information, physiological parameter information, and other information can be transferred from the IMD 105 to the external module 115, such as using a communicative coupling, such as a wireless telemetry link. The telemetered data can be used for analysis and interpretation either immediately or at a later time. In an example, at least one of the IMD 105 or the external module 115 can include a data storage circuit or a data processing circuit.

In an example, the external module 115 can include an antenna. In an example, the external module 115 can include a local medical device programmer or other local external module, such as within wireless communication range of the IMD 105 antenna. The external module 115 can include a remote medical device programmer or one or more other remote external modules (e.g., outside of wireless communication range of the IMD 105 antenna, but coupled to the IMD 105 using a local external device, such as a repeater or network access point). The external module 115 can include a processor circuit configured to process information that can be sent to or received from the IMD 105. The information can include medical device programming information, subject data, device data, or other instructions, alerts, or other information. In an example, the external module 115 can be configured to display information (e.g., received information) to a user. Further, the local programmer or the remote programmer can be configured to communicate the sent or received information to a user or physician, such as by sending an alert via email of the status of the subject 101 or the system 100 components.

Figure 2:
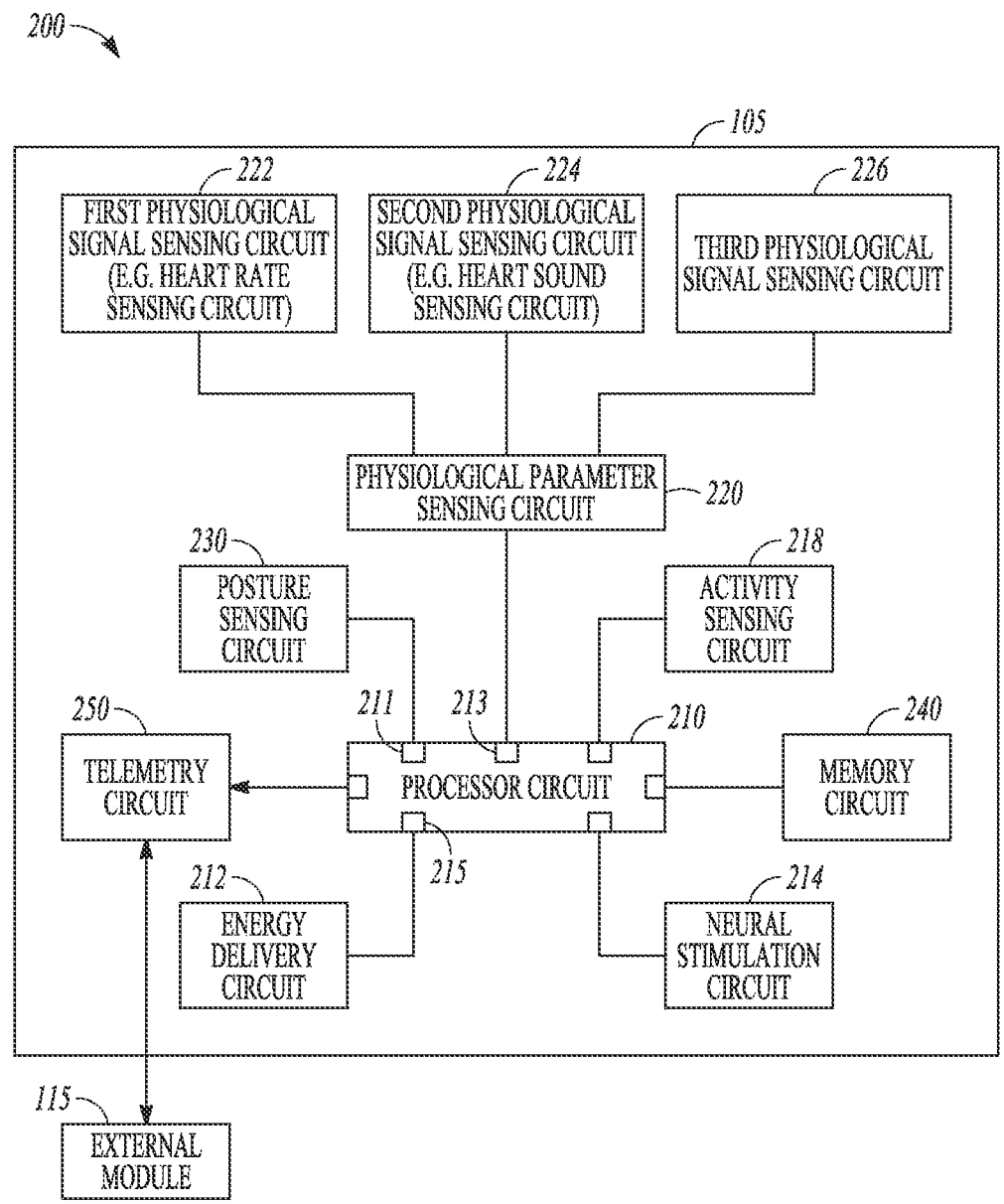
FIG. 2 illustrates generally an example of a portion of an implantable medical device including physiological signal sensing circuits, a processor circuit, therapy delivery circuits, or a telemetry circuit.

FIG. 2 illustrates generally a system 200 that can include the IMD 105 and the external module 115. The IMD 105 can include, among other elements, a processor circuit 210. In an example, the processor circuit 210 can include a first data input 211, a second data input 213, or a first data output 215, among other data inputs and outputs. In an example, the IMD 105 can include a posture sensing circuit 230 configured to provide posture information to the processor circuit 210 using the first data input 211. The posture sensing circuit 230 can use one or more physiological sensors, such as the sensor 106, to receive patient posture information. In an example, the posture sensing circuit 230 can include one or more of a tilt switch, a single axis accelerometer, or a multi-axis accelerometer.

In an example, patient posture information can include information that a patient is recumbent, seated, or upright, such as including standing lying down or standing postures. For example, a recumbent posture can include postures wherein a patient is tilted up less than 30 degrees from a horizontal position. An upright posture can include postures wherein a patient is tilted up more than 70 degrees from a horizontal position. Patient posture information can include information that a patient is recumbent, supine, prone, or is located intermediately between any of these positions. For example, patient posture information can include information that a patient is in a right or left recumbent posture. For example, a supine position can be defined to be a recumbent position at or near 0 degrees azimuth, or within a range of angles including zero degrees azimuth, for example between −45 degrees to +45 degrees. A left recumbent posture can be from about −45 degrees to about −135 degrees azimuth, while a right recumbent posture can be from about +45 degrees to about +135 degrees azimuth. A prone position can include positions such as within an azimuthal range of about −135 to about −180 degrees, or within an azimuthal range of about +135 to about +180 degrees. In an example, a postural change can be indicated at about a 20 degree change in tilt or azimuthal angle.

The processor circuit 210 can be coupled to a physiological parameter sensing circuit 220, such as can be configured to receive information from one or more physiological signal sensing circuits. For example, the physiological parameter sensing circuit 220 can receive information from at least one of a first physiological signal sensing circuit 222, a second physiological signal sensing circuit 224, or a third physiological signal sensing circuit 226, among others. In an example, the first physiological signal sensing circuit 222 can be configured to sense a patient heart rate. The second physiological signal sensing circuit 224 can be configured to sense heart sound activity. In an example, additional physiological signal sensing circuits can be used to sense other physiological signals, such as a stroke volume signal, a cardiac output signal, a blood oxygen concentration level signal, such as including a blood hemoglobin oxygen saturation level a blood carbon dioxide concentration level signal, a blood pressure signal, a heart sound signal such as a heart sound timing interval, a respiration rate signal, a thoracic impedance signal, or a lung tidal volume signal, or one or more other physiological signals.

In the example of FIG. 2, the processor circuit 210 can be coupled to one or more of an activity sensing circuit 218, a memory circuit 240, or a telemetry circuit 250. The processor circuit 210 can be configured to provide information to one or more therapy delivery sub-circuits, such as using one or more data outputs. For example, the first data output 215 can be configured to provide information to an energy delivery circuit 212, such as including defibrillation or pacing instructions. The energy delivery circuit 212 can include a pacing circuit, an anti-tachyarrhythmia pacing circuit, a cardiac resynchronization therapy circuit, or a defibrillation or cardioversion circuit, among others.

In an example, the IMD 105 can be configured to use the lead system 108 to receive physiological information or to provide stimulation energy to a patient body, such as to the heart 107. For example, one or more electrodes, such as included in the lead system 108, can be used to receive a thoracic impedance signal. The thoracic impedance signal can be received, such as using the third physiological signal sensing circuit 226. In an example, the physiological parameter sensing circuit 220 can be configured to extract one or more other physiological parameters from the thoracic impedance signal, such as a lung tidal volume, or a heart rate, or one or more others.

In an example, the physiological parameter sensing circuit 220 can be configured to receive physiological signal information at or near a detected change in posture. For example, the processor circuit 210 can coordinate the receipt of information from the posture sensing circuit 230 and the physiological parameter sensing circuit 220 such that physiological parameter information can be received before, during, or after a posture change. In an example, the physiological parameter sensing circuit 220 can be configured to obtain a transient signal representing one or more physiological parameters before, during, or after a posture change. The transient signal can be acquired continuously or at a sampling rate that can depend on the type of physiological signal to be received. For example, a heart rate signal can be sampled at about ten times per minute, or more often, depending on system features such as a capacity of the memory circuit 240 or the bandwidth available in the processor circuit 210. In an example, the transient signal can be acquired at multiple instances temporally near a change in posture status, such as determined using information received from the posture sensing circuit 230.

Figure 3:
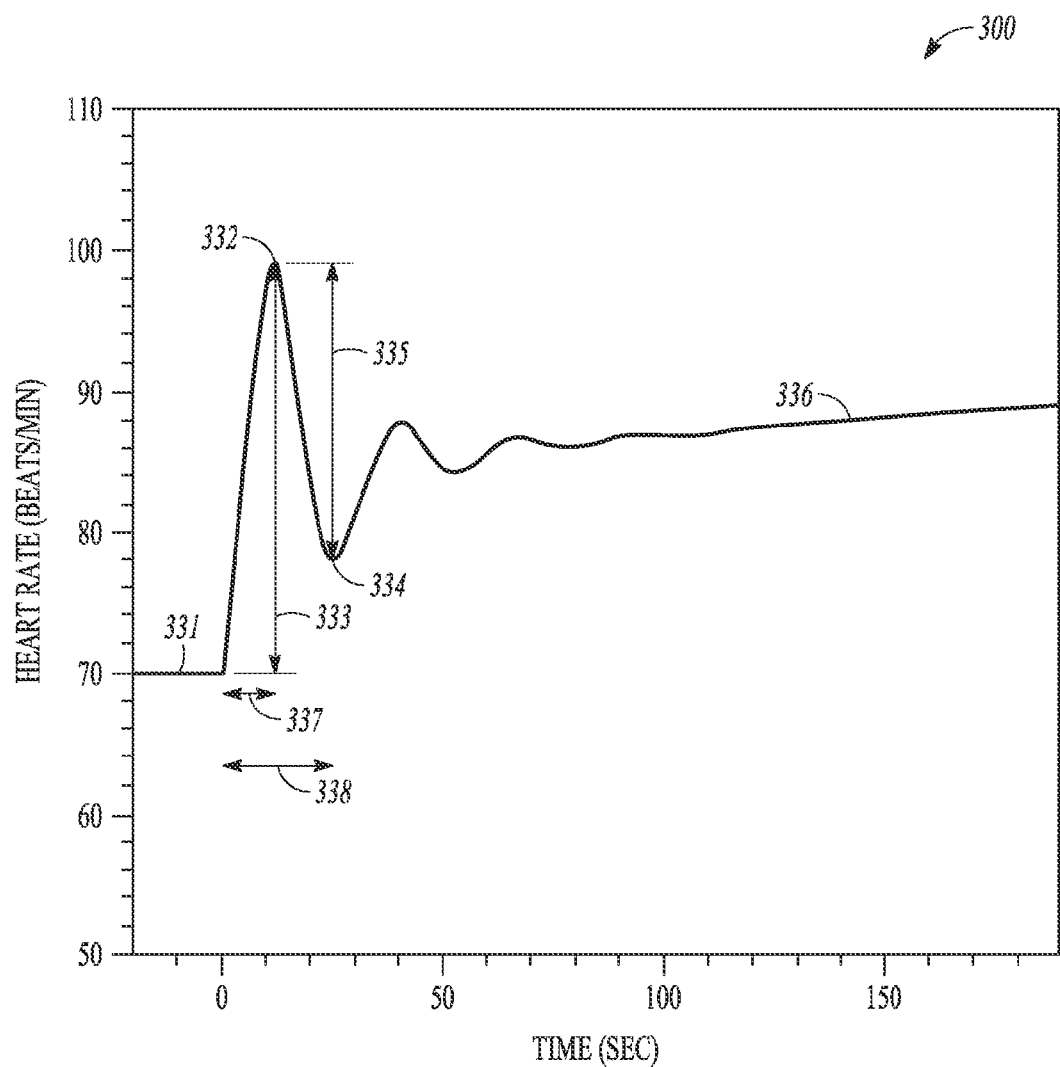
FIG. 3 illustrates generally an example of a transient signal.

FIG. 3 illustrates generally an example of a transient signal 300, such as a physiological signal, that can be received using one or more of the physiological signal sensing circuits, such as received by the physiological parameter sensing circuit 220. In the example of FIG. 3, the transient signal 300 can indicate a heart rate signal such as corresponding to a change in patient posture at t=0. For example, a posture change can be indicated using information received from the posture sensing circuit 230.

In the example of FIG. 3, the transient signal 300 can include one or more waveform morphology features, or several points of interest that can be used to determine the one or more waveform morphology features. For example, a baseline heart rate 331 can be indicated. In an example, a baseline heart rate can be about 70 beats per minute. In response to a posture change at time t=0, a patient heart rate can change, such as by increasing or decreasing. In the example of FIG. 3, the patient heart rate signal can increase, such as to attain a maximum or peak heart rate 332. In the example of FIG. 3, the peak heart rate 332 can be about 100 beats per minute. A transient increase in heart rate 333, $\Delta HR_{peak}$, can be a difference between the peak heart rate 332 and the baseline heart rate 331 (e.g., about 30 beats per minute). A first heart rate trough 334 can be a minimum heart rate recorded after the peak heart rate 332 (e.g., about 78 beats per minute), such as before a heart rate recovery period (e.g., after about t=50 seconds). A decrease in heart rate after peak 335 can be the difference between the peak heart rate 332 and the first heart rate trough 334 (e.g., about 22 beats per minute). A steady state heart rate after posture change 336 can be a new heart rate maintained by a patient, such as about 180 seconds after the posture change at t=0 (e.g., about 87 beats per minute). A time to maximum heart rate, or rise time 337, can be a duration from t=0 to the peak heart rate 332 (e.g., in the example of FIG. 3, about 10 seconds). A duration of an initial heart rate transient 338 can be a duration from t=0 to the first heart rate trough 334 (e.g., about 25 seconds). In the example of FIG. 3, a waveform morphology feature can include, among others, any one or more of the baseline heart rate 331, the peak heart rate 332, the transient increase in heart rate 333, the first heart rate trough 334, the decrease in heart rate after peak 335, the steady state heart rate after posture change 336, the rise time 337, or the duration of the initial heart rate transient 338.

Additional waveform morphology features can be derived from this or other transient signals, such as other transient signals representative of physiological signals. In an example, a waveform morphology feature can be derived from a transient signal representative of a blood pressure signal received at or near a posture change. In an example, a waveform morphology feature can be derived from, among other physiological signals, a heart rate signal, stroke volume signal, a cardiac output signal, a blood oxygen concentration level signal such as including a blood hemoglobin oxygen saturation level, a blood carbon dioxide concentration level signal, a heart sound signal, such as a heart sound timing interval, a respiration rate signal, a thoracic impedance signal, or a lung tidal volume signal, such as received at or near a posture change.

Other waveform morphology features, such as in addition to those described in the discussion of FIG. 3, are also determinable. For example, a waveform morphology feature can be derived using inflection points of the transient signal. In another example, a waveform morphology feature can represent a portion of transient signal peak, such as a width at half maximum, or a width at some other portion of a maximum. A waveform morphology feature can indicate a magnitude of change of a portion of a transient signal, or a duration of a portion of the transient signal, or a rate of change of a portion of the transient signal. In an example, a waveform morphology feature can include a duration of a portion of the transient signal, including a duration determined by a specified portion of a peak change of the transient signal. A waveform morphology feature can include other durations of portions of the transient signal, including a duration from a first specified portion of a post-posture-change transient response signal peak to a second specified portion of the post-posture-change transient response signal peak.

Figure 4A:
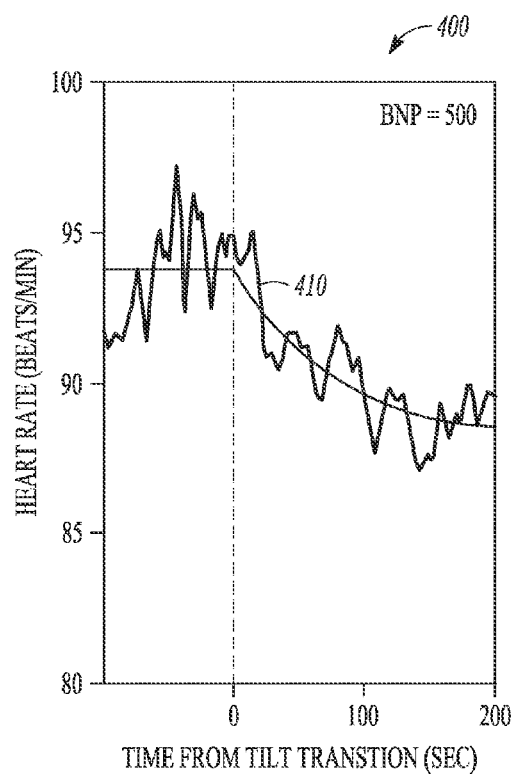
FIGS. 4A and 4B illustrate generally examples of a heart rate signal in response to a step posture change.
Figure 4B:
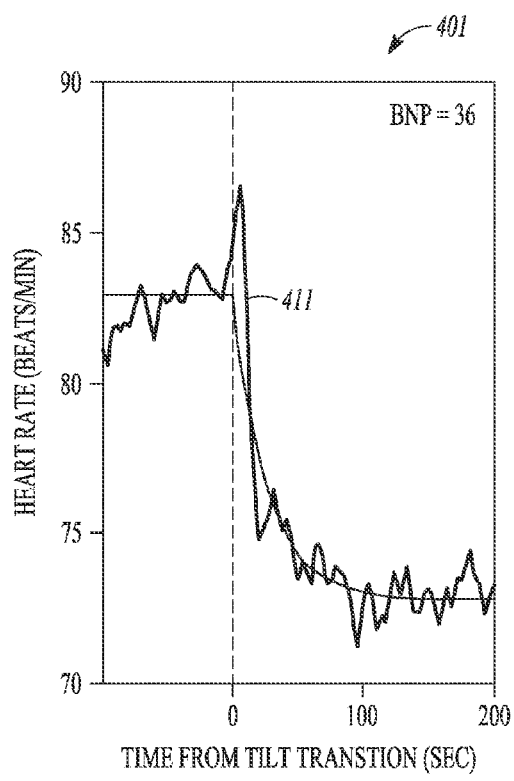

In an example, a waveform morphology feature, or set of waveform morphology features, can be analyzed such as to provide an indication of a healthy or diseased patient status, or to provide an indication of a worsening or improving heart failure condition. FIGS. 4A and 4B illustrate generally how a waveform morphology feature can be used to provide an indication of worsening heart failure. For example, in FIG. 4A, a first chart 400 can illustrate an example of a first heart rate signal 410 obtained at a posture change in a diseased patient. FIG. 4B illustrates generally a second chart 401, including an example of a second heart rate signal 411 obtained at a posture change in a healthy patient. In both the first chart 400 and the second chart 401, heart rate is represented on the vertical axis and time is represented on the horizontal axis. At time t=0, a patient posture change has occurred. The posture change can be a step posture change, such as from an upright to a recumbent posture.

In the example of FIG. 4A, the first chart 400 illustrates a diseased patient status, as indicated by an elevated brain natriuretic peptide (BNP) level of about 500 pg/mL. High levels of BNP can be associated with a decrease in cardiac output as compared to a normal patient status, and elevated levels of BNP can be correlated with an increased risk of a heart failure or decompensation event. In the example of FIG. 4A, the first heart rate signal 410 decreases in response to the posture change at t=0, such as a posture change from an upright to a recumbent posture. The first heart rate signal 410 decreases from a baseline heart rate of about 94 beats per minute to a steady state heart rate after posture change of about 88 beats per minute, a decrease of about 6%, after about 200 seconds.

In the example of FIG. 4B, the second chart 401 illustrates a normal patient status, with a BNP level of about 36 pg/mL. The second heart rate signal 411 decreases in response to the posture change at t=0, such as a posture change from the same upright posture to the same recumbent posture as illustrated in FIG. 4A in the chart 400. In the example of FIG. 4B, the second heart rate signal 411 decreases from a baseline heart rate of about 83 beats per minute to a steady state heart rate after posture change of about 73 beats per minute, a decrease of about 12%, after about 100 seconds.

In the examples of FIGS. 4A and 4B, a waveform morphology feature can include, among others, a heart rate decay magnitude or a heart rate decay duration. As illustrated in the first chart 400 and the second chart 401, the heart rate decay magnitude and heart rate decay duration can be correlated in patients with normal or elevated BNP levels. For example, a heart rate decay duration can be extended in patients with high BNP levels. A heart rate decay magnitude can be attenuated in patients with high BNP levels. In patients with normal or low BNP levels, a heart rate decay duration can be attenuated, and a heart rate decay magnitude can be greater than in a diseased patient state.

Figure 5:
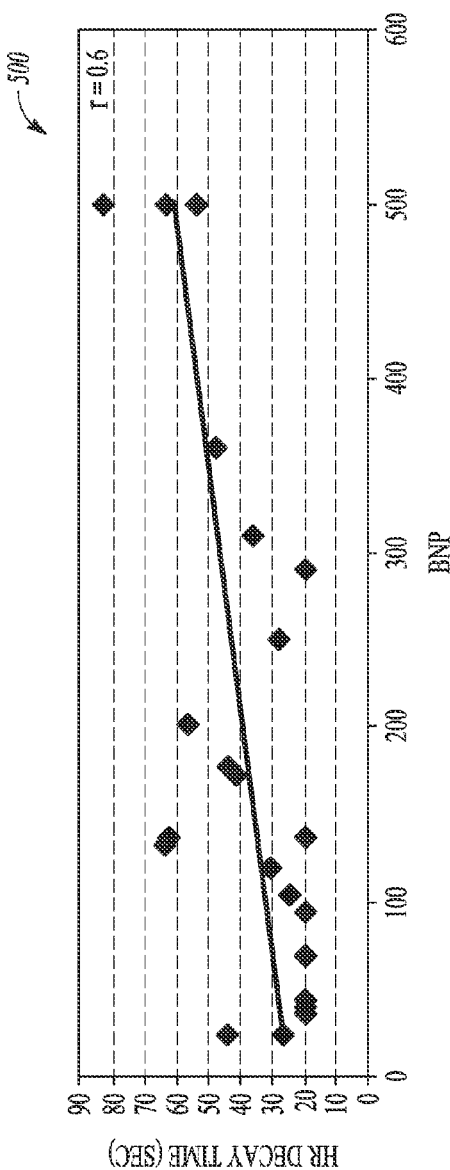
FIG. 5 illustrates generally an example of a correlation between a waveform morphology feature and BNP.

Waveform morphology features can be well-correlated with other predictors of heart failure. For example, heart rate decay time can be well-correlated with BNP level. FIG. 5 illustrates generally a chart 500 including a correlation between heart rate decay time and BNP level for multiple patients. For example, the chart 500 can indicate several patient BNP levels and associated heart rate decay time, such as for corresponding changes in posture, such as for about 27 patients. In the example of FIG. 5, a correlation coefficient r can be determined to be about 0.6, indicating a strong correlation between heart rate decay time and BNP level.

Figure 6:
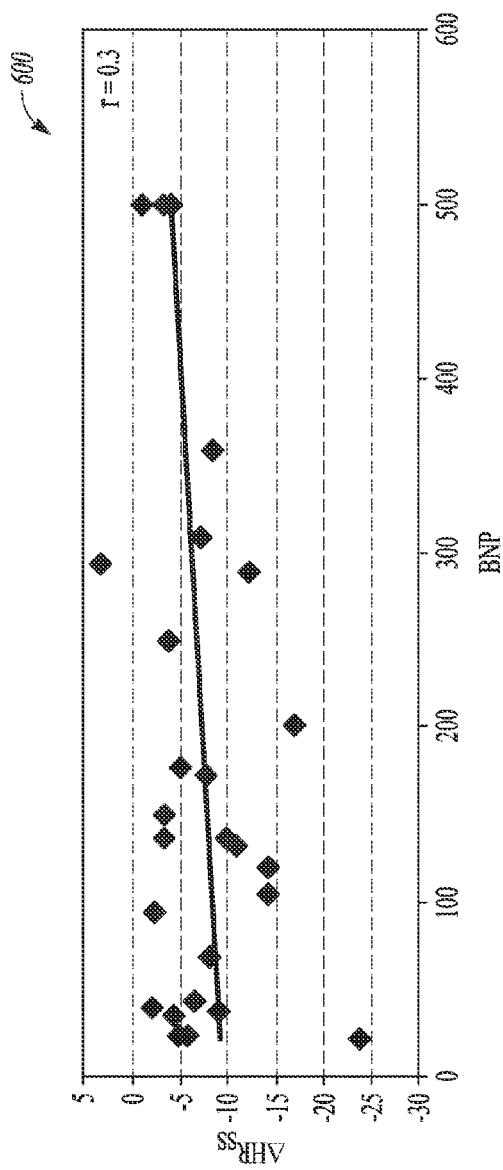
FIG. 6 illustrates generally an example of a correlation between a steady state physiological parameter and BNP.

In an example, a change in a steady state heart rate can be used to determine a heart failure status, such as described by Hatlestad et al., U.S. Patent Application No. 2008/0082001, entitled "PHYSIOLOGICAL RESPONSE TO POSTURE CHANGE," which is hereby incorporated herein by reference in its entirety. FIG. 6 illustrates generally a chart 600 including a correlation between a steady state change in heart rate, $\Delta HR_{ss}$, and BNP level for multiple patients. In the example of FIG. 6, a correlation coefficient r can be determined to be about 0.3, indicating a relatively weak correlation between $\Delta HR_{ss}$ and BNP level.

Figures 7A, 7B:
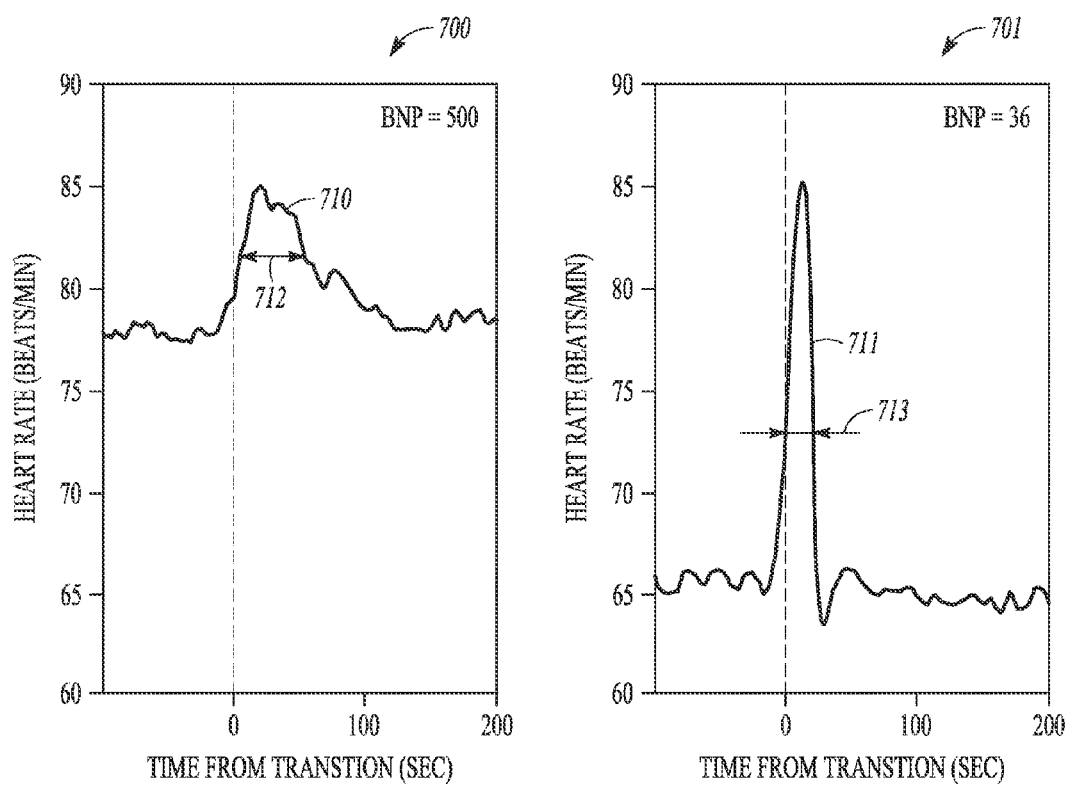
FIGS. 7A and 7B illustrate generally examples of a heart rate signal in response to an azimuthal angle posture change.

FIGS. 7A and 7B illustrate generally additional examples of waveform morphology features that can be used to provide an indication of worsening heart failure. For example, in FIG. 7A, a third chart 700 can illustrate an example of a third heart rate signal 710 obtained at a posture change in a diseased patient. In FIG. 7B, a fourth chart 701 can illustrate an example of a fourth heart rate signal 711 obtained at a posture change in a healthy patient. In both the third chart 700 and the fourth chart 701, heart rate is represented on the vertical axis and time is represented on the horizontal axis. At time t=0, a patient posture change has occurred. The posture change can be an azimuthal change among different, substantially recumbent postures, such as from a left recumbent posture to a supine posture.

In the example of FIG. 7A, the third chart 700 illustrates a diseased patient status, as indicated by an elevated BNP level of about 500 pg/mL. The third heart rate signal 710 increases in response to the posture change at t=0, such as a posture change among substantially recumbent postures. The third heart rate signal 710 increases from a baseline heart rate of about 77 beats per minute to a peak heart rate of about 85 beats per minute, and decays to a steady state heart rate after posture change of about 77 beats per minute. The peak heart rate indicates an increase of about 9%, and a width at half maximum 712 of about 30 seconds.

In the example of FIG. 7B, the fourth chart 701 illustrates a normal patient status, with a BNP level of about 36 pg/mL. The fourth heart rate signal 711 decreases in response to the posture change at t=0, such as a posture change among the same substantially recumbent postures as illustrated in the chart 700. In this example, the fourth heart rate signal 711 increases from a baseline heart rate of about 65 beats per minute to a peak heart rate of about 85 beats per minute. The heart rate rapidly decays to a steady state heart rate after posture change of about 65 beats per minute. The peak heart rate indicates an increase of about 30%, and a width at half maximum 713 of about 10 seconds.

In the examples of FIGS. 7A and 7B, a waveform morphology feature can include a heart rate decay magnitude, a rise time, a duration of an initial heart rate transient, or a width at half maximum, among others. As illustrated in the third chart 700 and the fourth chart 701, the width at half maximum can be correlated in patients with normal or elevated BNP levels. For example, in patients with elevated BNP levels, a width at half maximum 712 can be greater than a width at half maximum 713 in patients with a normal BNP levels.

Figure 8:
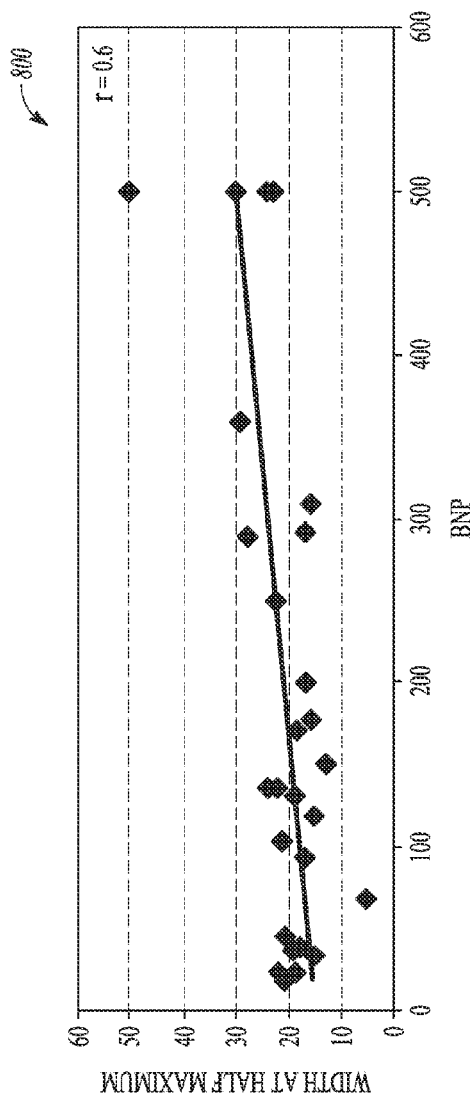
FIG. 8 illustrates generally an example of a correlation between a waveform morphology feature and BNP.

FIG. 8 illustrates generally a chart 800 including a correlation between width at half maximum and BNP level for multiple patients. For example, the chart 800 can indicate several patient BNP levels and corresponding widths at half maximum, such as for corresponding changes in posture, such as for about 27 patients. In the example of FIG. 8, a correlation coefficient r can be about 0.6, indicating a strong correlation between width at half maximum and BNP level.

Figure 9:
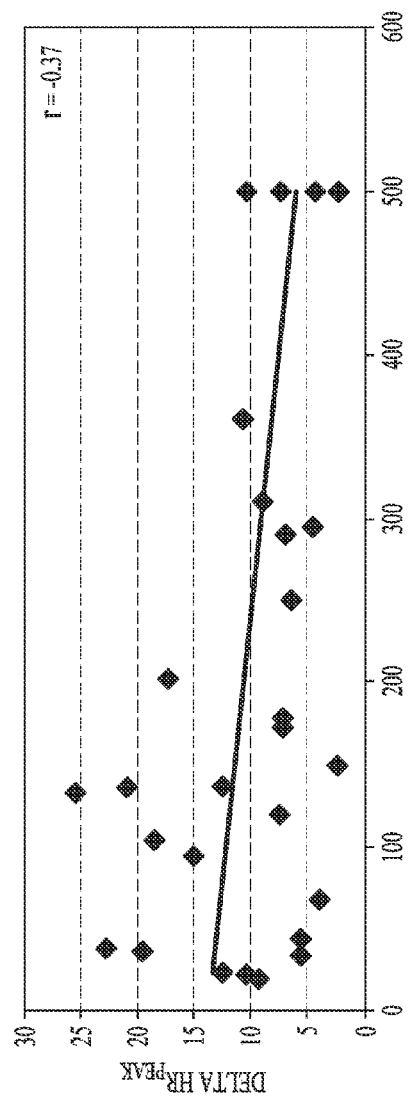
FIG. 9 illustrates generally an example of a correlation between a steady state physiological parameter and BNP.

FIG. 9 illustrates generally a chart 900 including a correlation between a magnitude change in peak heart rate and BNP level for multiple patients. For example, the chart 900 can indicate several patient BNP levels and corresponding changes in peak heart rate, such as for corresponding changes in posture. In the example of FIG. 9, a correlation coefficient r can be about −0.37, indicating a weak correlation between a magnitude change in peak heart rate and BNP level.

In an example, transient response signal data, such as can be obtained in response to changes in patient posture, can be received over multiple like-changes in patient posture. In an example, transient response signal data can be obtained during a patient's normal activities of daily life. For example, transient response signal data can be obtained for multiple like-changes in patient posture over the course of a portion of a day, an entire day, a week, or a month, etc. In an example, a waveform morphology feature can be extracted from the received transient response signal data, such as to enable analysis of time of the features.

Figure 10:
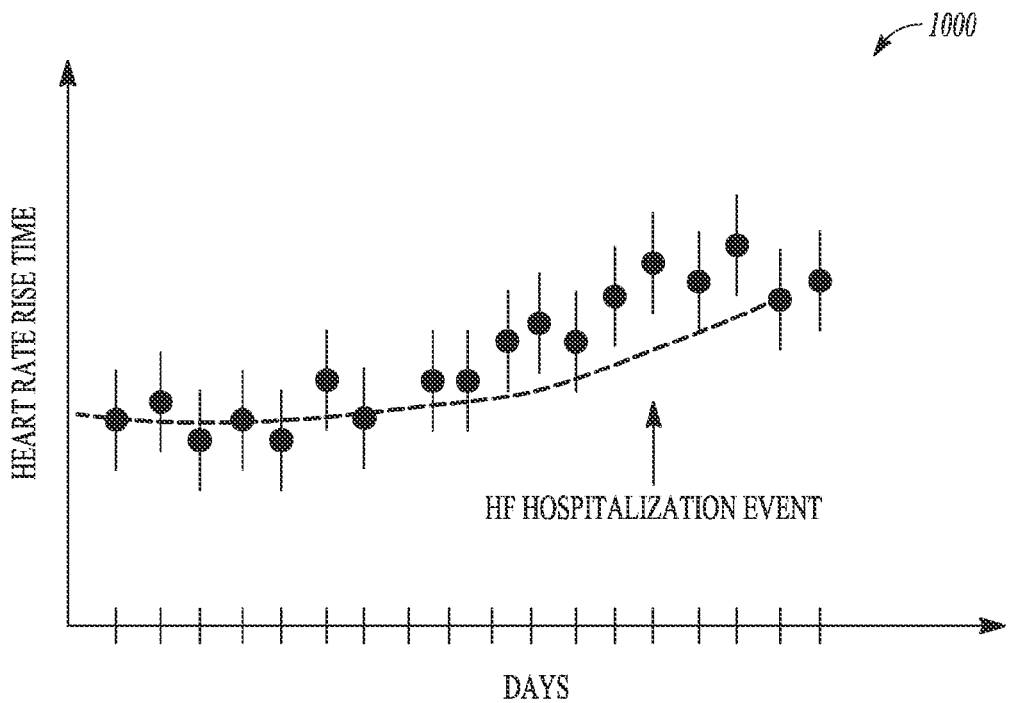
FIG. 10 illustrates generally an example of a trend of a waveform morphology feature.

FIG. 10 illustrates generally a trend 1000 of a waveform morphology feature. In the example of FIG. 10, heart rate rise time can be trended over a period of about 18 days. For each day and each like-change in posture, a central tendency, such as an average, of the heart rate rise time can be determined and trended. The heart rate rise time, among other waveform morphology features, can be extracted from a transient physiological signal indicative of heart rate, such as a thoracic impedance signal. In an example, the heart rate rise time can be extracted from a transient physiological signal derived from one or more heart sound signals.

The heart rate rise time information can be received from a transient signal representative of multiple like-changes in posture. For example, the trend 1000 can include data points representing a central tendency, such as mean or average heart rate rise time information corresponding to a posture change among at least two different, substantially recumbent, postures, such as during a single day. The trend 1000 can include standard deviation information, such as to provide an indication of the range of values a particular waveform morphology feature can attain. In the example of FIG. 10, a "normal" heart rate rise time can be indicated for the data received during the first several days. After the seventh day, the patient's heart rate rise time can increase, such as to indicate an increased likelihood of a heart failure or decompensation episode. Once the heart rate rise time reaches a certain threshold, a hospitalization event can be indicated.

Other trends of waveform morphology features can indicate improving cardiac health. For example, a decrease in heart rate rise time, such as over a period of several weeks or months, can indicate beneficial cardiac remodeling, such as in response to effective cardiac resynchronization therapy. In an example, a trend can be established for each posture change for which data are available. For example, a first trend can represent posture changes from substantially upright to substantially recumbent postures. A second trend can represent posture changes from substantially supine to substantially right recumbent. A third trend can represent posture changes from a first substantially left recumbent position to a second substantially left recumbent position.

In addition, a unique trend can be established for each waveform morphology feature for each type of posture change. For example, if two posture changes are used (e.g., a first posture change from a substantially recumbent posture to a substantially upright posture, and a second posture change from a substantially upright posture to a substantially recumbent posture), and two waveform morphology features are used (e.g., blood pressure rise time, and blood oxygen concentration level), then four trends can be established (e.g., a first trend corresponding to the first posture change and the blood pressure rise time; a second trend corresponding to the second posture change and the blood pressure rise time; a third trend corresponding to the first posture change and the blood oxygen concentration level; and a fourth trend corresponding to the second posture change and the blood oxygen concentration level). The number of possible trends can be limited, for example, by system capacity, or an ability of the posture sensing circuit 230 to discriminate among different postures. In an example, one or more trends can be used to indicate a diseased or improving patient status, such as a heart failure status. The trends can be used to provide an indication of worsening or improving patient health status, including in patients with chronic obstructive pulmonary disease (COPD), or in diseases other than congestive heart failure which are correlated with BNP, among other diseases.

Figure 11:
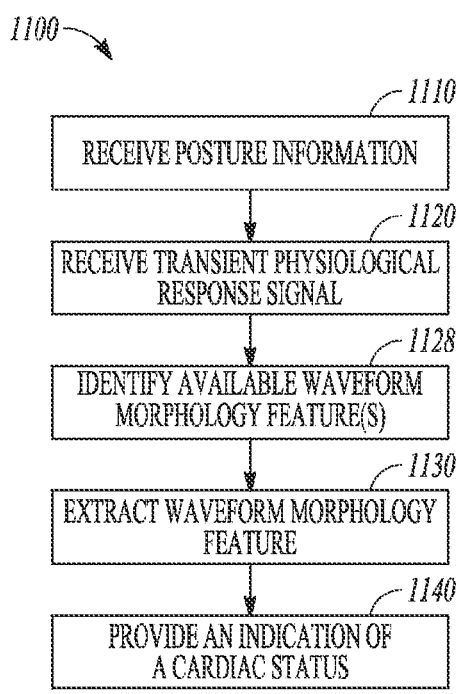
FIG. 11 illustrates generally an example that can include receiving posture information, receiving a transient physiological response signal, extracting a waveform morphology feature, and providing an indication of a cardiac status.

FIG. 11 illustrates generally an example that can include providing an indication of a cardiac status. For example, posture information can be received at 1110. The posture information can be received from, among other sensors, a multi-axis accelerometer, such as using the posture sensing circuit 230 disposed in the IMD 105. In an example, the sensor 106 can be configured to receive posture information. In an example, the posture sensing circuit 230 can receive thoracic impedance information, such as can be used to provide posture information according to Thakur et al., U.S. Patent Application No. 61/423,128, entitled "POSTURE DETECTION USING THORACIC IMPEDANCE," which is hereby incorporated herein by reference in its entirety. Thakur et al. describe, among other things, clustering thoracic impedance information, and discerning posture information using quantitative attributes associated with one or more of the clusters.

At 1120, physiological signal information can be received, such as a transient physiological response signal indicative of a physiological signal. The physiological signal can indicate a change in patient physiology. For example, the transient physiological response signal can include a thoracic impedance signal, such as can be obtained using one or more implantable or surface electrodes disposed in or on a body. The thoracic impedance signal can indicate various physiological changes, such as a heart contraction, a lung tidal volume, or a respiration rate, among others. In an example, the transient physiological response signal can include information about a stroke volume or cardiac output signal, such as can be derived using thoracic impedance information. The transient physiological response signal can include a heart rate signal, or a heart sound signal, such as can be obtained using one or more microphones or accelerometers to identify and discriminate among, for example, S1 and S2 heart sounds. The transient physiological response signal can include a blood pressure signal, a heart rate signal or a heart rate variability signal, such as can be derived from a pressure sensor (e.g., the sensor 106) disposed in a heart or coronary vein, among other locations. The transient physiological response signal can include information about a blood oxygen concentration or a blood carbon dioxide concentration, such as can be received using a blood chemistry analysis circuit coupled to the physiological parameter sensing circuit 220. Other transient physiological response signals, such as in response to a posture change, can be used as well.

At 1128, one or more waveform morphology features can be identified, such as corresponding to a waveform morphology of the transient physiological response signal received at 1120. For example, a set of available waveform morphology features can be identified (e.g., a rise time, a width or duration at half maximum, a decay time, or any other waveform morphology feature that can be descriptive of a behavior of at least a portion of a transient signal, as described above), such as corresponding to at least a portion of the transient physiological response signal. In an example, the number or type of identifiable waveform morphology features can be determined at least in part by a particular detected change in posture. For example, a first set of waveform morphology features (e.g., including rise time and decay time) can be identified for a step change in posture, or a second set of waveform morphology features (e.g., including an initial transient duration, and a magnitude of an initial transient) can be identified for an azimuthal change in posture.

At 1130, a waveform morphology feature can be extracted, such as from the transient physiological response signal received at 1120. In an example, any of the waveform morphology features discussed above, such as in the discussion of FIG. 3, can be extracted from the transient physiological response signal. For example, if the transient physiological response signal indicates a transient blood pressure signal, a waveform morphology feature, such as extracted at 1130, can include a blood pressure rise time or a blood pressure decay time. In an example, an attenuated transient response in a diseased patient state, as compared to a healthy patient state, can represent chronotropic incompetence, which can be reflected in one or more waveform morphology features, such as a rise time. In an example, the waveform morphology feature extracted at 1130 can include a waveform morphology feature identified at 1128, such as can correspond to a particular change in posture.

At 1140, an indication of a cardiac status can be provided, such as using the waveform morphology feature extracted at 1130. In an example, a waveform morphology feature, such as a blood pressure rise time, can be compared with a waveform morphology feature threshold or metric. An increased patient risk of heart failure can be indicated where a blood pressure rise time exceeds some threshold rise time, or exceeds a baseline rise time associated with a particular patient.

Figure 12:
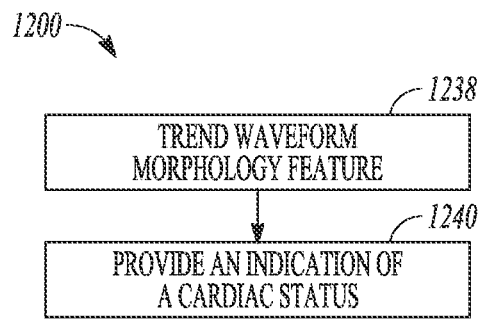
FIG. 12 illustrates generally an example of trending a waveform morphology feature and providing an indication of a cardiac status.

FIG. 12 illustrates generally an example that can include trending a waveform morphology feature. For example, at 1238, a waveform morphology feature, such as extracted at 1130, can be trended. The waveform morphology feature can be trended according to the discussion of FIG. 10. In the example of FIG. 12, a trend of a waveform morphology feature, or multiple waveform morphology features, such as corresponding to one or more changes in posture, can be used to provide an indication of a cardiac status at 1240. In an example, the indication of a cardiac status provided at 1240 can include an indication of worsening heart failure, or can include an indication of beneficial cardiac remodeling, or can include an indication that a patient is maintaining a constant cardiac health status.

In an example, the indication of a cardiac status provided at 1240 can include an indication of an efficacy of autonomic modulation therapy (AMT). For example, successful AMT can be indicated in strong transient responses, which can be represented by the extracted waveform morphology features. Such features can be trended, and analyzed, such as to provide an indication of a cardiac status at 1240. In an example, the indication of a cardiac status provided at 1240 can include an indication of an efficacy of a cardiovascular therapy, such as a device therapy (e.g., a cardiac resynchronization therapy) or a drug therapy (e.g., beta blockers, angiotensin-converting enzyme (ACE) inhibitors, anti-arrhythmic medications, etc.).

Figure 13:
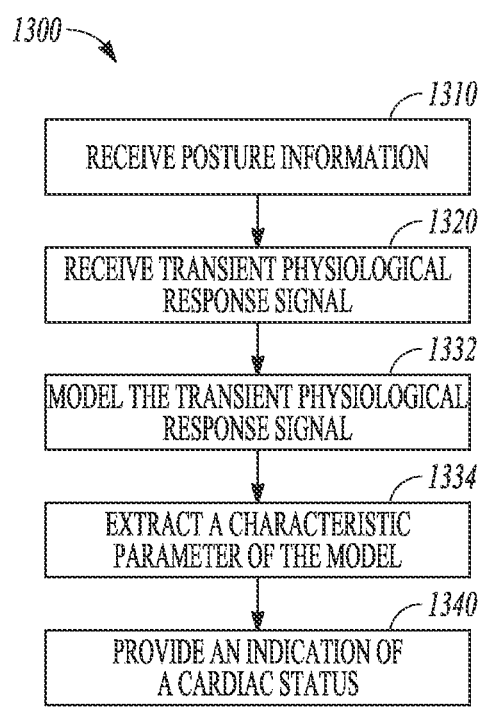
FIG. 13 illustrates generally an example that can include receiving posture information, receiving a transient physiological response signal, modeling the transient physiological response signal, extracting a characteristic parameter of the model, and providing an indication of a cardiac status.

FIG. 13 illustrates generally an example that can include modeling a transient signal and providing an indication of a cardiac status. For example, posture information can be received at 1310, such as according to the discussion at 1110. A transient physiological response signal can be received, such as in response to a posture change. For example, the response signal can be received according to the discussion at 1120.

In an example, the transient physiological response signal can be modeled at 1332, such as to fit a first- or second-order system response signal. In an example, the dynamics of the transient response signal can be modeled and approximated using a first-order differential equation, such as $$\tau \frac{dy}{dt} + y(t) = f(t),$$

where the system is defined by the parameter τ, the system time constant, and ƒ(t) is a forcing function. In an example, the dynamics of the transient response signal can be modeled and approximated using a second-order differential equation, such as to capture information about oscillatory behavior.

At 1334, a characteristic parameter can be extracted from the model. For example, where a second-order system model is used to model the transient physiological response signal, the characteristic parameter can include an undamped natural frequency, or a damping ratio, among other parameters (e.g., a delay duration, a magnitude change of a portion of the transient physiological response signal, etc.). At 1340, an indication of a cardiac status can be provided, such as according to the discussion at 1140. In an example, one or more of the characteristic parameters extracted from the model can be used in a manner similar to the waveform morphology features. For example, a characteristic parameter can be compared to a threshold or metric, or can be trended, such as over a period of several days or weeks, such as to observe a trend in the characteristic parameter. In an example, a natural frequency of oscillation can be trended over a period of several weeks. For example, a natural frequency of oscillation can be derived from a transient physiological response signal indicative of a blood pressure signal. In this example, a decrease in the natural frequency of oscillation, such as compared to a baseline patient natural frequency of oscillation, can indicate a worsening cardiac health status, such as an increased risk of heart failure.

SPECIFIC ILLUSTRATIVE EXAMPLES

Hemodynamic responses to orthostatic tilt can be blunted in congestive heart failure (HF) patients, as discussed above. A relationship between a transient response to postural change and patient HF status can be measured, such as using BNP. In an example, heart rate and posture data can be collected from multiple ambulatory HF patients. A multi-axis accelerometer, such as can be signal processed to obtain continuous, patient-specific posture information using tilt and azimuthal angle information, can be used to identify multiple classes of postural transitions. In an example, the accelerometer can register a postural change, such as with several seconds of a steady-state posture on either side of a transition. In an example, classes of postural transitions can include recumbent to upright, upright to recumbent, or transitions between left or right recumbent and supine postures. In an example, a beat-by-beat heart rate segment can be obtained, such as using surface EKG, temporally near each transition, and averaged across one or more transitions of a given class. Patient BNP can be averaged, such as before, during, and after the heart rate monitoring, such as to compare with transient heart rate responses.

In an example, chronic data from multiple patients over multiple weeks can yield an average number of transitions of about 37 (e.g., Max: 132; Min: 1) for recumbent to upright transitions, about 35 (e.g., Max: 117; Min: 3) for upright to recumbent transitions, or about 122 (e.g., Max: 407; Min: 9) for left or right recumbent to supine transitions, such as with about 5 minutes of steady state postures on either side of the transition. A heart rate decrease (e.g., ΔHR=−7.25±5.6 bpm) during upright to recumbent postural transitions can be non-significantly correlated (e.g., r=0.31; p=0.11), but a rate of decay, such as defined as the time to reduce ΔHR by 50%, can be significantly correlated to BNP (e.g., r=0.6; p<0.005). In an example, the rise time during recumbent to upright postural transitions can be less well-correlated to BNP (e.g., r=0.11), although the correlations of steady state change (e.g., ΔHR=6.67±4.47 bpm) can be comparable (e.g., r=0.28; p=0.17). In an example, some left or right recumbent to supine postural transitions can be associated with a transient rise in HR, such as followed by a return to a steady state heart rate. In an example, a peak change, such as of a transient rise from baseline (e.g., ΔHR=10.52±6.43), can be correlated to BNP (e.g., r=−0.37; p=0.06), or the width of a transient change (e.g., temporal width at 50% ΔHR) can be correlated with BNP (e.g., r=0.6; p<0.005). In this example, a time course of transient heart rate responses, such as corresponding to postural transitions, such as from upright to recumbent postures or left or right recumbent to supine postures, among others, can be extracted from heart failure patients with ambulatory monitoring devices. Such time course information can be correlated with patient-specific BNP levels and can serve as a monitor of heart failure status.

ADDITIONAL NOTES & EXAMPLES

Example 1 includes subject matter, such as a medical device, comprising a processor, including a first data input, configured to receive information indicative of a change in posture status, and a second data input, configured to receive, at multiple instances temporally near the change in posture status, a transient response signal of a physiological parameter in response to the change in posture status. For example, the transient response signal can indicate a patient physiological response to the posture change. Example 1 can include subject matter such as a processor-readable medium, including instructions that, when performed by the processor, configure the medical device to extract a waveform morphology feature from the transient response signal, and provide an indication of a cardiac status using the extracted waveform morphology feature.

In Example 2, the subject matter of Example 1 can optionally include a a first data input configured to receive information indicative of a change in posture status. For example, the change in posture status can include a posture change between a substantially recumbent posture and a substantially upright posture. In an example, the change in posture status can include a posture change between a first substantially recumbent posture and a different, second substantially recumbent posture.

In Example 3, the subject matter of one or any combination of Examples 1-2 can optionally include a second data input configured to receive, at multiple instances temporally near the change in posture status, a transient response signal of a physiological parameter in response to the change in posture status, wherein the physiological parameter can include, among others, a heart rate, a blood pressure, a heart sound metric, a heart rate variability, a blood oxygen concentration, a blood carbon dioxide concentration, a respiration rate, a thoracic impedance, or a lung tidal volume.

In Example 4, the subject matter of one or any combination of Examples 1-3 can optionally include a processor-readable medium including instructions that, when performed by the processor, configure the apparatus to extract a waveform morphology feature from the transient response signal, wherein the extracted waveform morphology feature can indicate, among other things, a magnitude of change of a portion of the transient response signal, or a duration of a portion of the transient response signal.

In Example 5, the subject matter of one or any combination of Examples 1-4 can optionally include a processor-readable medium including instructions that, when performed by the processor, configure the apparatus to provide an indication of a cardiac status using the extracted waveform morphology feature, wherein the indication of a cardiac status can indicate, among other things, a heart failure status, a chronotropic incompetence status, an effectiveness of autonomic modulation therapy, or an effectiveness of a cardiovascular therapy.

In Example 6, the subject matter of one or any combination of Examples 1-5 can optionally include a processor-readable medium including instructions that, when performed by the processor, configure the apparatus to provide an indication of a cardiac status using a trend of an extracted waveform morphology feature over multiple like-changes in patient posture status.

In Example 7, the subject matter of one or any combination of Examples 1-6 can optionally include a processor-readable medium including instructions that, when performed by the processor, configure the apparatus to provide an indication of a cardiac status using a multiple-day trend of an extracted waveform morphology feature. In Example 7, the waveform morphology feature can be determined using a central tendency, such as can be computed over multiple like-changes in posture status.

In Example 8, the subject matter of one or any combination of Examples 1-7 can optionally include a processor-readable medium including instructions that, when performed by the processor, configure the apparatus to provide an indication of a cardiac status using a multiple-day trend of the extracted waveform morphology feature, wherein the waveform morphology feature can be determined using a central tendency over multiple like-changes in patient posture status, such as from a substantially recumbent posture to a substantially upright posture.

In Example 9, the subject matter of one or any combination of Examples 1-8 can optionally include a processor-readable medium including instructions that, when performed by the processor, configure the apparatus to extract a waveform morphology feature from the transient response signal, wherein the waveform morphology feature can include at least one of a delay duration, a decay duration, a natural frequency of oscillation, or a magnitude change of a portion of the transient response signal. Example 9 can optionally include providing an indication of a cardiac status using at least one of the delay duration, the decay duration, the natural frequency of oscillation, or the magnitude change of a portion of the transient response signal.

In Example 10, the subject matter of one or any combination of Examples 1-9 can optionally include a processor-readable medium including instructions that, when performed by the processor, configure the apparatus to compare a waveform morphology feature to a metric, and provide an indication of a cardiac status, including an indication of a heart failure status, using the comparison.

Example 11 can include, or can be combined with the subject matter of one or any combination of Examples 1-10 to optionally include receiving information indicative of a change in posture status, receiving, at multiple instances temporally near a change in posture status, a transient response signal of a physiological parameter in response to a change in posture status, extracting a waveform morphology feature from a transient response signal, or providing an indication of a cardiac status using the extracted waveform morphology feature.

In Example 12, the subject matter of one or any combination of Examples 1-11 can optionally include receiving, at multiple instances temporally near a change in posture status, a transient response signal of a physiological parameter in response to a change in posture status, such as including receiving a transient response signal indicative of at least one of a posture change between a substantially recumbent posture and a substantially upright posture, or a first substantially recumbent posture and a different, second substantially recumbent posture.

In Example 13, the subject matter of one or any combination of Examples 1-12 can optionally include receiving, at multiple instances temporally near the change in posture status, a transient response signal of a physiological parameter in response to a change in posture status, such as including receiving a transient response signal of a physiological parameter, the physiological parameter including, among other parameters, a heart rate, a blood pressure, a heart sound metric, a heart rate variability, a blood oxygen concentration, a blood carbon dioxide concentration, a respiration rate, a thoracic impedance, or a lung tidal volume.

In Example 14, the subject matter of one or any combination of Examples 1-13 can optionally include extracting a waveform morphology feature from a transient response signal, including extracting, from the transient response signal, a magnitude of change of the transient response signal, or a duration of a portion of the transient response signal.

In Example 15, the subject matter of one or any combination of Examples 1-14 can optionally include providing an indication of a cardiac status using an extracted waveform morphology feature, such as including providing, among others, an indication of a heart failure status, a chronotropic incompetence status, an effectiveness of autonomic modulation therapy, or an effectiveness of a cardiovascular therapy.

In Example 16, the subject matter of one or any combination of Examples 1-15 can optionally include providing an indication of a cardiac status using the extracted waveform morphology feature, including providing an indication of a cardiac status using a trend of an extracted waveform morphology feature over multiple like-changes in posture status.

In Example 17, the subject matter of one or any combination of Examples 1-16 can optionally include providing an indication of a cardiac status, such as using a trend, including providing an indication of a cardiac status using a multiple-day trend of the extracted waveform morphology feature, wherein the waveform morphology feature can be determined using a central tendency, such as can be computed over multiple like-changes in posture status.

Example 18 can include, or can be combined with the subject matter of one or any combination of Examples 1-17 to optionally include determining a characteristic parameter of a transient response signal. Example 18 can optionally include a characteristic parameter such as a delay duration, a decay duration, a natural frequency of oscillation, or a magnitude change of a portion of the transient response signal. Example 18 can optionally including providing an indication of a cardiac status using the characteristic parameter.

In Example 19, the subject matter of one or any combination of Examples 1-18 can optionally include providing an indication of a cardiac status using a characteristic parameter, such as by comparing the characteristic parameter to a metric, and providing the indication of a cardiac status, including an indication of a heart failure status, using the comparison.

In Example 20, the subject matter of one or any combination of Examples 1-19 can optionally include a processor circuit, including a first data input configured to receive information indicative of a change in posture status, or a second data input configured to receive, at multiple instances temporally near the change in posture status, a transient response signal of a physiological parameter in response to a change in posture status. Example 20 can include subject matter such as a processor-readable medium, including instructions that, when performed by a processor, can configure the apparatus to model the transient response signal as a first or second order system response signal, extract a characteristic parameter of the modeled first or second order system signal, the characteristic parameter including at least one of a delay duration, a decay duration, a natural frequency of oscillation, or a magnitude change of a portion of the system response signal, or provide, such as using the extracted characteristic parameter, an indication of worsening heart failure. These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:
1. A system, comprising:
   a first sensor configured to detect a change in posture status;
   a second sensor configured to sense a transient response signal of a physiological parameter during the change in posture status;
   a processor circuit, configured to generate a cardiac status based on the transient response signal of the physiological parameter, the transient response signal occurring during the change in posture status; and
   a monitoring circuit configured to provide an indication of the cardiac status.
2. The system of claim 1, wherein the second sensor is configured to sense a transient response of a heart rate (HR) signal before and during the change in posture status, the transient response of the HR signal including on or more of:
   a transient increase in HR from a baseline HR prior to the posture change to a peak HR during the change in posture status;
   a decrease in HR from the peak HR to a first HR trough after the peak HR during the change in posture status;
   a duration for the HR to rise from the baseline HR to the peak HR during the change in posture status; or
   a duration of an initial HR transient from the baseline HR to the first HR trough.

3. The system of claim 1, wherein the processor circuit is configured to generate the cardiac status based on waveform morphology of at least a portion of the transient response signal.

4. The system of claim 3, wherein the waveform morphology includes a rise time, a decay time, or a duration of the at least a portion of the transient response signal.

5. The system of claim 3, wherein:
the first sensor is configured to determine the detected change in posture status as one of a plurality of classes of posture changes including a step change or an azimuthal change in posture; and
the processor circuit is configured to generate the cardiac status based at least on the determined class of change in posture status.

6. The system of claim 5, wherein the plurality of classes of postural changes include a change between recumbent and upright postures, or a change between recumbent and supine postures.

7. The system of claim 1, wherein the processor circuit is configured to generate the cardiac status based on one or more characteristic parameters of a signal model representing the transient response signal.

8. The system of claim 7, wherein:
the signal model includes a first or second order system approximation of a waveform morphology of the transient response signal; and
the one or more characteristic parameters include at least one of a delay duration, a decay duration, a natural frequency of oscillation, or a magnitude change extracted from the signal model.

9. The system of claim 1, wherein the first sensor includes at least one of a tilt switch, a single axis accelerometer, or a multi-axis accelerometer.

10. The system of claim 1, wherein:
the processor circuit is configured to extract from the transient response signal one or more signal features occurring during the change in posture status, and to establish respective trends of the one or more signal features over a specified period of time, each of the respective trends indicating worsening or improving patient health status; and
the monitoring circuit is configured to display the respective trends.

11. The system of claim 1, wherein the processor circuit is configured to generate respective cardiac status before and after delivery of one of a cardiovascular therapy, an autonomic modulation therapy, or a drug therapy.

12. The system of claim 1, further comprising a therapy delivery circuit configured to deliver a therapy based at least on the cardiac status.

13. A method, comprising:
detecting a change in posture status of a patient;
sensing a transient response signal of a physiological parameter during the change in posture status;
generating a cardiac status based on the transient response signal of a physiological parameter, the transient response signal occurring during the change in posture status; and
providing an indication of the cardiac status.

14. The method claim 13, wherein sensing the transient response signal includes sensing a transient response of a heart rate (HR) signal before and during the change in posture status, the transient response of the HR signal including on or more of:
a transient increase in HR from a baseline HR prior to the posture change to a peak HR during the change in posture status;
a decrease in HR from the peak HR to a first HR trough after the peak HR during the change in posture status;
a duration for the HR to rise from the baseline HR to the peak HR during the change in posture status; or
a duration of an initial HR transient from the baseline HR to the first HR trough.

15. The method of claim 13, wherein generating the cardiac status includes generating the cardiac status based on waveform morphology of at least a portion of the transient response signal.

16. The method of claim 13, wherein:
detecting the change in posture status includes classifying the detected posture change as one of a plurality of classes of posture changes including a step change or an azimuthal change in posture; and
generating the cardiac status includes generate the cardiac status based at least on the determined class of change in posture status.

17. The method of claim 13, wherein generating the cardiac status includes creating a signal model to represent the transient response signal, and generating the cardiac status based on one or more characteristic parameters of the signal model.

18. The method of claim 17, wherein:
the signal model includes a first or second order system approximation of a waveform morphology of the transient response signal; and
the one or more characteristic parameters include at least one of a delay duration, a decay duration, a natural frequency of oscillation, or a magnitude change extracted from the signal model.

19. The method of claim 13, further comprising:
extracting from the transient response signal one or more signal features occurring during the change in posture status;
establishing respective trends of the one or more signal features over a specified period of time, each of the respective trends indicating worsening or improving patient health status; and
displaying the respective trends.

20. The method of claim 13, wherein generating the cardiac status includes generating respective cardiac status before and after delivery of a therapy including a cardiovascular therapy, an autonomic modulation therapy, or a drug therapy, the cardiac status indicating an efficacy of the delivered therapy.

* * * * *